US00PP32243P2

(12) United States Plant Patent
Hansen

(10) Patent No.: US PP32,243 P2
(45) Date of Patent: Sep. 29, 2020

(54) ***LAGERSTROEMIA* PLANT NAMED 'PERKY PINK'**

(50) Latin Name: ***Lagerstroemia* (L.) hybrid**
Varietal Denomination: 'Perky Pink'

(71) Applicant: Hans A Hansen, Zeeland, MI (US)

(72) Inventor: Hans A Hansen, Zeeland, MI (US)

(73) Assignee: Walters Gardens Inc, Zeeland, MI (US)

( * ) Notice: Subject to any disclaimer, the term of this patent is extended or adjusted under 35 U.S.C. 154(b) by 0 days.

(21) Appl. No.: 16/873,024

(22) Filed: Jan. 15, 2020

(51) Int. Cl.
*A01H 5/02* (2018.01)

(52) U.S. Cl.
USPC ..... Plt./252

(58) Field of Classification Search
USPC ..... Plt./252
See application file for complete search history.

*Primary Examiner* — Annette H Para

(57) ABSTRACT

The new and distinct Crape Myrtle plant named *Lagerstroemia* 'Perky Pink' has a dense mounded habit, that is ground hardy to at least USDA zone 6, has matte, dark olive-green foliage that have a mahogany color when young. The pink flowers on densely-branched reddish stems cover the shrub. The new plant resists leaf spot and powdery mildew and is useful in the landscape as a specimen, en masse, or as a container plant.

1 Drawing Sheet

Botanical classification: *Lagerstroemia* (L.) hybrid.
Variety denomination: 'Perky Pink'.

STATEMENT REGARDING PRIOR DISCLOSURES UNDER 37 CFR 1.77(B)(6)

The first public disclosure of the claimed plant, in the form of a photograph and brief description on a website operated by Walters Gardens, Inc. was on Feb. 1, 2019. Subsequently, on May 29, 2019 Walters Gardens, Inc. advertised the new plant in the "Walters Gardens 19-20 Catalog" and by the first sale on Apr. 17, 2019. Walters Gardens, Inc. obtained the plant and all information relating thereto, from the inventor. No plants of *Lagerstroemia* 'Perky Pink' have been sold in this country or anywhere in the world, nor has any disclosure of the new plant been made, more than one year prior to the filing date of this application, and such sale or disclosure within one year was either derived directly or indirectly from the inventor.

BACKGROUND OF THE INVENTION

The present invention relates to a new and distinct cultivar of *Lagerstroemia* plant, commonly known as Crape Myrtle, and hereinafter referred to by the cultivar name 'Perky Pink' or the "new plant." 'Perky Pink' is grown primarily as an ornamental for landscape use and for use as a potted plant, and is the result of an ongoing breeding program to produce new and improved garden worthy plants for the ornamental plant market. The new plant was the result of open-pollinated seed collected by the inventor in fall of 2012 in a trial garden facility at a wholesale perennial nursery in Zeeland, Mich., USA using the proprietary, unreleased, unnamed hybrid known only by the breeder code H10-08-01 (not patented) as the seed or female parent. The male or pollen parent is a sibling of H10-08-01 (not patented). The new plant was given the breeder code 12-29-6.

*Lagerstroemia* 'Perky Pink' was initially asexually propagated by stem cuttings at a wholesale perennial nursery in Zeeland, Mich., USA in 2014. The resultant plants from successive generations have demonstrated that the new plant has remained stable and true to type in multiple and successive generations of asexual propagation.

SUMMARY OF THE INVENTION

Plants of the new cultivar 'Perky Pink' have not been observed under all possible environmental conditions. The phenotype may vary somewhat with changes in light, temperature, soil and available moisture and fertility without, however, any variance in genotype.

The following traits have been repeatedly observed and are determined to be unique characteristics of 'Perky Pink'. Among the characteristics in combination which distinguish 'Perky Pink' as a new and distinct cultivar, unique from all other cultivars known to the inventor are:

1. Dense, mounded growth habit;
2. Matte foliage emerges mahogany-colored and matures to dark olive-green;
3. Lower stems are striated, reddish-brown and tan-colored with upper stems reddish;
4. Pink flowers in dense panicles open on new growth to cover the shrub;
5. Resistance to *Cercospora* leaf spot and *Erisphe* powdery mildew;
6. Ground hardy to at least USDA hardiness zone 6.

The most similar cultivars known to the inventor include: 'Chaff Berry' U.S. Plant patent application Ser. No. 16/350,860, 'Dark Roast' U.S. Plant patent application Ser. No. 16/350,861 and the copending U.S. Plant patent application Ser. No. 16/873,023 'Peppermint Mocha'. 'Dark Roast' is shorter in habit and the flowers are a different hue of bright fuchsia pink. 'Chai Berry' is slightly taller and more upright in habit and the flowers are a different hue of rose-pink. 'Peppermint Mocha' has a shorter slightly more spreading habit and the flowers are a more rosy-pink. The female parent H10-08-01 has flowers are a more lavender coloration. Comparison with the male parent is not possible since the male parent was not maintained.

BRIEF DESCRIPTION OF THE DRAWINGS

The accompanying color photographs illustrate the flower and foliage characteristics and the overall appearance of a seven-year-old plant of 'Perky Pink', growing in a full-sun trial garden in Zeeland, Mich., showing the colors as true as it is reasonably possible to obtain in color reproductions of this type. Colors in the photographs may differ slightly from the color values cited in the detailed botanical description which accurately describe the colors of the new *Lagerstroemia*.

DETAILED BOTANICAL DESCRIPTION

Figure 1:
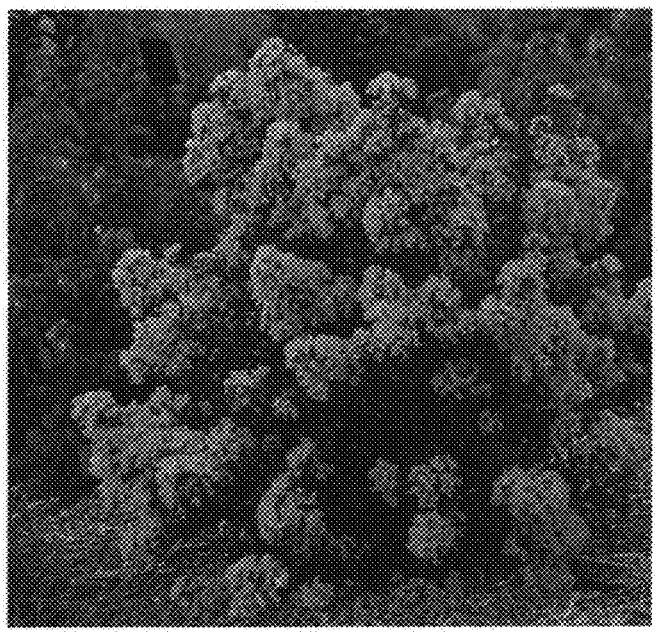
FIG. 1 shows a plant in a full-sun trial garden in late summer peak flowering.
Figure 2:
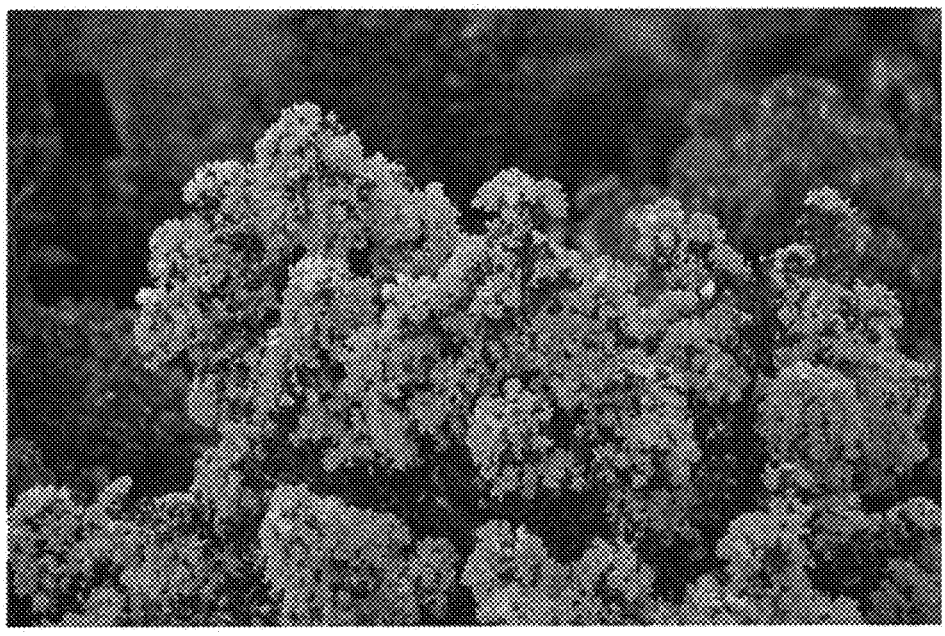
FIG. 2 shows a close-up for the flowers and buds.

The following color references are based on the 2015 edition of The Royal Horticultural Society Colour Chart except where common dictionary terms are used. The following observations and size descriptions are of approximately seven-year-old plants grown in a loamy-sand, full-sun, open trial bed in Zeeland, Mich., USA with supplemental water and fertilizer as needed. The phenotype may vary slightly with different environmental conditions, such as temperature, light, fertility, moisture and maturity levels, but without any change in the genotype.

Botanical classification: *Lagerstroemia* (L.) hybrid; Parentage: female, or seed parent the unnamed, unreleased hybrid H10-08-01; the male, or pollen parent is a sibling of H10-08-01;

Propagation: Terminal softwood stem cuttings;

Time to initiate roots: About three weeks;

Growth rate: Moderate; finishing from a 65 mm liner in a 3.7 liter container in about 10 to 14 weeks in the summer season;

Plant description: Deciduous, woody, narrow, compact flowering shrub; about six mainly upright to outward primary stems; freely branched;

Root description: Fine, numerous, fibrous, well-branched;

Plant habit: Compact, rounded mound; about 75.0 cm high from the soil level to the top of the inflorescences; about 70.0 cm wide with no pinching, pruning or plant growth regulators;

Stems: About eight; to about 62.0 cm long and about 16.0 mm diameter at base; young stems cylindrical with four longitudinal carinae, along line on either side of petioles; basal stems cylindrical with slightly exfoliating bark; highly branched with about 12 alternate branches, lower branches held nearly horizontal and upper branches held at about a 45 degree angle above horizontal; branches to about 30.0 cm long and 5.0 mm diameter at base;

Stem color: Woody basal portion striated with over wintered stems nearest RHS 177B and nearest RHS 200A; young developing stems striated with nearest RHS 183B and RHS 177B;

Node: About 32 to 45 per main stem; internode length average about 1.5 cm in main stems;

Node color: Same as surrounding stem;

Foliage description: Sub-opposite to alternate; simple; ovate; margin entire to micro-ciliolate; flat; apex broadly acute; aequilateral, rounded base; adaxial micro-puberulent, matte; abaxial sparsely micro-puberulent, matte; to about 45.0 mm long and 28.0 mm wide, average about 40.0 mm long and 24.0 mm wide;

Abaxial leaf color: Young emerging—adaxial nearest RHS 187A, abaxial nearest RHS 187B; mature—adaxial RHS NN137A without blush, abaxial nearest RHS 138A;

Veins: Pinnate; micro-puberulent adaxial and abaxial;

Vein color: Young emerging—adaxial midrib nearest RHS 187B, abaxial midrib nearest RHS 187B; mature—adaxial midrib nearest RHS 146D and secondary veins nearest RHS NN137B, abaxial midrib and secondary veins nearest RHS 145C with light blush of nearest RHS 187C;

Petiole: Typically sessile, rarely very short; glabrous; up to 1.0 mm long and 2.0 mm wide; color adaxial nearest RHS 187B and abaxial nearest RHS 187B;

Inflorescence: Panicle; terminal branched panicles up to about 300 flowers; average about 250 flowers; up to about 30.0 cm long and about 25.0 cm across; beginning late-summer and continuing for up to four weeks;

Buds: Globose to ellipsoidal; very slightly carinate; with rounded apex and rounded base; lustrous; glabrous; about 11.0 mm long and about 8.0 mm diameter one day prior to opening; longitudinal suture lines of weak prominence;

Bud color: Exposed petals blend between RHS 61C and RHS NN155D; calyx base nearest RHS, distally nearest RHS 187A;

Flowers: Perfect; regular; actinomorphic; stalked; held in terminal panicle; individually about 33.0 mm across and about 22.0 mm long to tip of exserted anthers; corolla to about 18.0 mm long; lasting about two days;

Flower fragrance: Faintly sweet;

Peduncle: Cylindrical with four longitudinal carinae in proximal portion and cylindrical in distal portion; about 5.0 mm diameter at base below lowest flowering branch, to about 30.0 cm long and 25.0 cm across;

Peduncle color: Nearest RHS 183B;

Pedicel: Cylindrical; glabrous; lustrous; about 6.0 mm long and 1.0 mm diameter;

Pedicel color: Between RHS 183B to RHS 187B;

Calyx: Fused to form hypanthium; campanulate; 9.0 mm long and 8.0 mm across;

Sepals: Fused in about the basal 6.0 mm; acute apex, entire margin; glabrous and lustrous both adaxial and abaxial; about 9.0 mm long and individually and about 4.0 mm wide at fusion point;

Sepal color: Adaxial basal portion nearest RHS NN155B, distal portion nearest RHS 182C; abaxial nearest RHS 187B;

Petals: Six; stalked; glabrous; blade ruffled or crisped; margin crisped; blade with rounded apex and auriculate base, to about 18.0 mm across and 12.0 mm long; claw base or stalk adnate to calyx, to about 9.0 mm long and 0.7 mm diameter; overall about 18.0 mm long;

Petal color: Blade adaxial and abaxial nearest RHS N66C; claw more white than RHS 51D;

Androecium:

*Stamens*.—Typically about 42; six longer and about 36 shorter.

*Filaments*.—Cylindrical; shorter stamens to about 12.0 mm long and about 0.1 mm diameter, curved to twisted; longer filaments arcuate in distal 5 mm, about 20.0 mm long and about 0.5 mm diameter; color of shorter filaments between RHS 54B and RHS 54C.

*Anthers*.—Only on longer filaments; dorsifixed; ellipsoid; more developed on longer stamens to about 1.5 mm long and 1.2 mm across; color nearest RHS 8A.

*Pollen*.—Abundant on longer stamens; color nearest RHS 14A.

Gynoecium: One; about 27.0 mm long;

*Style*.—Cylindrical; glabrous; about 23.5 mm long and 0.5 mm diameter; color nearest RHS 53B.

*Stigma*.—Globose; lustrous; about 0.5 mm diameter; color between RHS 177A and RHS 177B.

*Ovary*.—Superior; ellipsoidal; lustrous; about 3.0 mm tall and 2.0 mm diameter; color nearest RHS 162D.

*Fruit*.—Globose; dehiscent, loculicidal, penta-valved capsule; about 7.0 mm across and 9.0 mm tall; immature color nearest RHS 145C, mature color nearest RHS 165A.

Seed: Typically 12 to 25 seeds per fruit; winged; to about 6.0 mm long and 3.0 mm across and 1.5 mm thick at embryo; color between RHS 199C and RHS N199C at embryo and RHS 164D in wing;

Disease resistance: *Lagerstroemia* 'Perky Pink' has shown resistance to powdery mildew and black leaf spot, *Erisphe* and *Cercospora* fungi, respectively. Other resistance beyond that typical for crape myrtle has not been observed. The new plant's root system is capable of withstanding cold temperatures typical of those found in USDA zone 6.

It is claimed:

1. A new and distinct cultivar of Crape Myrtle, *Lagerstroemia* plant named 'Perky Pink' essentially as herein illustrated and described.

* * * * *